United States Patent [19]

Largman et al.

[11] 4,044,001
[45] Aug. 23, 1977

[54] PROCESS FOR PREPARING α-CHLORO-ε-CAPROLACTAM

[75] Inventors: Theodore Largman, Morris Township; Stylianos Sifniades, Madison, both of N.J.

[73] Assignee: Allied Chemical Corporation, Morris Township, N.J.

[21] Appl. No.: 720,013

[22] Filed: Sept. 2, 1976

[51] Int. Cl.$^2$ .......................................... C07D 223/10
[52] U.S. Cl. ............................................. 260/239.3 R
[58] Field of Search ................................ 260/239.3 R

[56] References Cited

U.S. PATENT DOCUMENTS

| 2,877,220 | 3/1959 | O'Neill et al. | 260/239.3 R |
|---|---|---|---|
| 3,757,007 | 9/1973 | Fujita et al. | 260/239.3 R |
| 3,767,648 | 10/1973 | Fujita et al. | 260/239.3 R |

Primary Examiner—Henry R. Jiles
Assistant Examiner—Robert T. Bond
Attorney, Agent, or Firm—Robert J. North; Robert A. Harman

[57] ABSTRACT

A process is described for preparing α-chloro-ε-caprolactam, an intermediate for the synthesis of L-lysine, comprising reacting an N-substituted -α-chloro-ε-caprolactam, wherein the N-substituent is an organic radical selected from the group consisting of arylsulfonyl, aroyl and alkanoyl radicals, with ε-caprolactam at a temperature within the range of about 50° to about 250° C to form α-chloro-ε-caprolactam and an N-substituted-ε-caprolactam. A continuous process is also described for the production of α-chloro-ε-caprolactam further comprising the chlorination of N-substituted-ε-caprolactam to produce N-substituted-α-chloro-ε-caprolactam.

23 Claims, No Drawings

PROCESS FOR PREPARING α-CHLORO-ε-CAPROLACTAM

BACKGROUND OF THE INVENTION

1. Field of the Invention

This invention relates to a process for preparing α-chloro-ε-caprolactam which is a useful intermediate in the synthesis of L-lysine from ε-caprolactam. L-lysine is an essential amino acid and is a necessary part of the diet of certain mammals. α-Chloro-ε-caprolactam is also a useful monomer in producing chlorine-containing nylon polymers.

2. Brief Description of the Prior Art

ε-Caprolactam has long been recognized as a potential starting material for making sythetic L-lysine. One synthetic scheme for making L-lysine from ε-caprolactam involves the chlorination of ε-caprolactam to form α-chloro-εcaprolactam, which is treated with ammonia to form α-amino-ε-caprolactam, which then may be subjected to a resolution-racemization technique as described in U.S. Pat. No. 3,941,776 to recover L-α-amino-ε-caprolactam, which is in turn hydrolyzed to L-lysine. A major problem with this particular synthetic approach to L-lysine starting with ε-caprolactam is presented by the first step, i.e. the chlorination of ε-caprolactam to form α-chloro-ε-caprolactam. Direct chlorination of ε-caprolactam usually leads to the α,α-dichloro-ε-caprolactam, which then must be reduced to form the α-chloro-ε-caprolactam. This is an economically unattractive procedure. Various other methods have been described in the literature for the direct chlorination of ε-caprolactam but they suffer from either chlorination of the nitrogen atom, low yields, require expensive solvents, or are poorly reproducible.

However, the chlorination of N-benzoyl-ε-caprolactam to N-benzoyl-α-chloro-ε-caprolactam in good yield is known in the prior art as exemplified in U.S. Pat. No. 3,096,325 (March 1963).

Exchange reactions involving ε-caprolactam or its derivatives are not well known and are only briefly described in the prior art. A caprolactam derivative is described as taking part in an exchange reaction involving an organic radical in the synthesis of ε-caprolactam and 0-acetyl-cyclohexanone oxime from the transfer of an acetyl group from N-acetyl-ε-caprolactam to cyclohexanoneoxime (Fujita, et al., U.S. Pat. No. 3,767,648). N-acyl-ε-caprolactams are reported to be efficient acylating agents for amines, [Ramos, et al., Anales real soc. espan. fis. & Chim. (Madrid) 56B, 833 (1956)]. A linear polyamide (Nylon 6) has also been shown to undergo transamidation in a very specialized case with acetamide as reported by the above authors in the same journal volume 52B, 735–8 (1956). However, a transamidation reaction occurring between two different caprolactam molecules is not known in the prior art.

It is an object of this invention to provide a process for preparing α-chloro-ε-caprolactam by a transamidation reaction between N-substituted-α-chloro-ε-caprolactam and ε-caprolactam.

It is a further object of this invention to provide a continuous process for preparing α-chloro-ε-caprolactam by a transamidation reaction between N-substituted-α-chloro-ε-caprolactam and ε-caprolactam.

SUMMARY OF THE INVENTION

In accordance with the present invention, there is provided a process for preparing α-chloro-ε-caprolactam which comprises reacting an N-substituted-α-chloro-ε-caprolactam, wherein the N-substituent is an organic radical selected from the group consisting of arylsulfonyl, aroyl and alkanoyl radicals, with ε-caprolactam to form α-chloro-ε-caprolactam and N-substituted-ε-caprolactam. The reaction will ordinarily be carried out at a temperature within the range of about 50° to about 250° C. The reactants may be reacted neat or in the presence of up to about 20 times their combined weight of an inert organic solvent.

The reaction of the present invention is thought to proceed as follows:

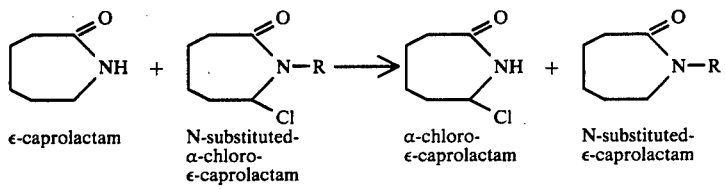

ε-caprolactam  N-substituted-α-chloro-ε-caprolactam  α-chloro-ε-caprolactam  N-substituted-ε-caprolactam There is also provided a continuous process for preparing α-chloro-ε-caprolactam which comprises reacting an N-substituted-α-chloro-ε-caprolactam, wherein the N-substituent is an organic radical selected from the group consisting of arylsulfonyl, aroyl and perhalogenated alkanoyl radicals, with ε-caprolactam. The reaction will ordinarily be carried out at a temperature within the range of about 50° to about 250° C. in the presence of an inert water immiscible organic solvent in an amount of up to about 20 times the combined weight of the reactants, N-substituted-α-chloro-ε-caprolactam and ε-caprolactam. The α-chloro-ε-caprolactam product can be recovered from the reaction mixture usually by extraction with aqueous acid, and the by-product N-substituted-ε-caprolactam in the organic solvent is chlorinated to produce the reactant N-substituted-α-chloro-ε-caprolactam and recycled back into the reaction mixture, as illustrated by the following equations:

(1) Chlorination:

N-substituted ε-caprolactam + SO₂Cl₂ → α-chloro-N-substituted-ε-caprolactam + SO₂ + HCl (2) Transamidation

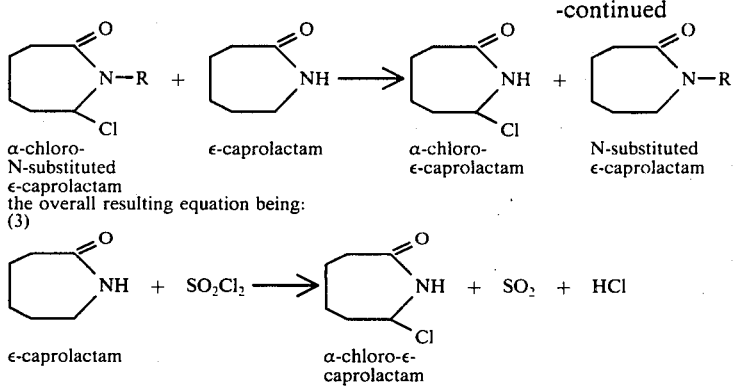

α-chloro-N-substituted ε-caprolactam + ε-caprolactam → α-chloro-ε-caprolactam + N-substituted ε-caprolactam the overall resulting equation being:
(3)

ε-caprolactam + SO$_2$Cl$_2$ → α-chloro-ε-caprolactam + SO$_2$ + HCl

DETAILED DESCRIPTION OF THE INVENTION AND PREFERRED EMBODIMENTS

The invention as herein described relates to a general process to produce α-chloro-ε-caprolactam from ε-caprolactam via a transamidation process and may also further involve the chlorination of N-substituted-ε-caprolactam to form N-substituted-α-chloro-ε-caprolactam and its recycle constituting a continuous process for producing α-chloro-ε-caprolactam.

The advantage of the present invention is embodied in the fact that N-substituted-α-chloro-ε-caprolactam surprisingly enters into a transamidation reaction with ε-caprolactam very readily. This allows the preparation of α-chloro-ε-caprolactam in high yield from ε-caprolactam obviating all of the difficulties previously mentioned involved in the direct chlorination of ε-caprolactam.

The term transamidation reaction as used herein refers to the transfer of an organic radical R affixed to the nitrogen atom of an amide molecule, the donor molecule, to the nitrogen atom of a second amide molecule, the donee molecule. In general, the transfer is reversible and an equilibrium is established during the reaction.

Suitable organic radicals as N-substituent groups herein designated R are those which migrate easily from N-substituted-α-chloro-ε-caprolactam to ε-caprolactam during the transamidation reaction and include arylsulfonyl, aroyl and alkanoyl radicals.

Examples of arylsulfonyl radicals that are suitable are those containing 6 to 10 carbon atoms and include p-tosyl (p-methylbenzenesulfonyl), benzenesulfonyl, p-chlorobenzenesulfonyl and 2,4-dichlorobenzenesulfonyl. Preferred arylsulfonyl radicals are p-tosyl, p-chlorobenzenesulfonyl and benzenesulfonyl.

Examples of alkanoyl radicals that are suitable are those containing 1 to 4 carbon atoms and include acetyl, propionyl and butanoyl. Preferred among the alkanoyl radicals is the acetyl.

Examples of aroyl radicals that are suitable are those containing 7 to 12 carbon atoms and are illustrated by the following formula:

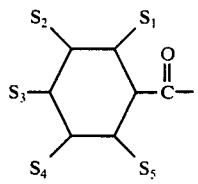

wherein S is a ring substituent and wherein $S_1$ to $S_5$ can be the same or different and are selected from the group consisting of hydrogen, chlorine, nitro, trifluoromethyl and nitrile. Preferred embodiments are those where $S_1$ and $S_5$ are both are hydrogen, and the remaining substituents are the same or different and are selected from the group consisting of chlorine, nitro, trifluoromethyl and nitrile. The most preferred embodiment is where $S_1$ to $S_5$ are hydrogen and the radical is benzoyl.

Where a continuous process is desired, then the radical chosen must be also inert to chlorination under the reaction conditions. For this reason it is preferred to use benzenesulfonyl, and p-chlorobenzenesulfonyl among the arylsulfonyl radicals and p-chlorobenzoyl, p-nitrobenzoyl and benzoyl among the aroyl radicals. Since the alkanoyl radicals are readily susceptible to chlorination under the reaction conditions it is preferred to use perhalogenated alkanoyl radicals. Among those most preferred are trichloroacetyl and trifluoroacetyl.

Usually, an inert organic solvent is used in the process to dissolve the reactants to conduct the reaction, but the reaction can also be conducted neat, in the molten state, by melting the reactants to initiate the reaction. It is preferred, however, to use an inert organic solvent to conduct the reaction, and where a continuous process is desired, the solvent must also be water immiscible.

Solvents which are useful in the practice of the method of the present invention are those which are inert under the reaction conditions. Exemplary inert solvents include aliphatic and aromatic ethers, aliphatic hydrocarbons, aromatic hydrocarbons, aliphatic halocarbons and aromatic halocarbons. Examples of aliphatic ethers that can be used are those containing 4 to 10 carbon atoms including dipropyl ether, dibutyl ether, and the cyclic aliphatic ethers, tetrahydrofuran and dioxane. Preferred ethers that are used are dioxane and tetrahydrofuran. Aromatic ethers that are preferred are biphenyl ether and a mixture of biphenyl ether and biphenyl.

Examples of aliphatic hydrocarbons that are suitable are those containing 5 to 20 carbon atoms including petroleum ether and the higher boiling aliphatic hydrocarbons, with boiling points of about 50° C. to 250° C. Aromatic hydrocarbons that can be utilized are those including 6 to 18 carbon atoms including benzene, toluene, xylene, naphthalene and alkyl-substituted naphthalenes. Preferred among the aromatic hydrocarbons are xylene, either the ortho, meta or para isomers or mixtures thereof.

Examples of halogenated aliphatic hydrocarbons that are suitable are those containing 1 to 10 carbon atoms and include carbon tetrachloride, chloroform, dichloroethane, perchloroethylene and dichlorobutane. Examples of halogenated aromatic hydrocarbons that can be used are those containing 6 to 18 carbon atoms and 1 to 4 chlorine atoms and include chlorobenzene, ortho, meta and para-dichlorobenzene, trichlorobenzene and parachloroxylene. Preferred among the halogenated aromatic hydrocarbons is ortho-dichlorobenzene.

The solvent chosen should be a suitable solvent for the starting N-substituted-α-chloro-ε-caprolactam and ε-caprolactam. A preferred solvent for this purpose is xylene whose solvent properties also permit the precipitation of N-substituted-α-chloro-ε-caprolactam upon cooling thereby providing a convenient method of separating starting materials from the reaction mixture. The transamidation reaction of the invention is conducted at a temperature within the range of about 50° to about 250° C., preferably within the range of about 100° to about 160° C. The weight ratio of solvent used per weight of N-substituted-α-chloro-ε-caprolactam is usually within the range from about 10 to 1 parts solvent per part of N-substituted-α-chloro-ε-caprolactam and a preferred range being from about 5 to 1 parts by weight of solvent per part of the N-substituted-α-chloro-ε-caprolactam.

The transamidation can also be conducted under pressure utilizing a solvent of the classes of solvents discussed herein and the modifications with respect to temperature and time and optimal reaction conditions will be obvious to one skilled in the art.

Time required for efficient conversion in the reaction is a function of both the temperature and the solvent used and also of the amounts of starting materials employed. By efficient conversion is meant choosing and regulating the reaction conditions such that a high degree of transfer of the organic radical occurs between the donor and donee caprolactam molecules before equilibrium in the reaction is established. For example, a preferred embodiment of the transamidation reaction is the reaction of N-benzoyl-α-chloro-ε-caprolactam with ε-caprolactam in xylene at 140° C. for 2 hours, in which the molar ratio of N-benzoyl-α-chloro-ε-caprolactam to ε-caprolactam is 2:1, in which a 70 to 80% conversion of N-benzoyl-α-chloro-ε-caprolactam to α-chloro-ε-caprolactam is achieved. In general, the invention practiced utilizing the embodiments described herein will require a conversion time within the range from about a half hour to 10 hours and a more preferred range being from 2 hours to 6 hours before equilibrium is established.

In a continuous type of process advantage is taken of the fact that the N-substituted-α-chloro-ε-caprolactam, especially in the case of N-benzoyl-α-chloro-ε-caprolactam, is relatively insoluble in xylene and ortho-dichlorobenzene upon cooling. Therefore, in order to increase the percent conversion of ε-caprolactam in the transamidation reaction, an excess of the N-benzoyl-α-chloro-ε-caprolactam is used which can subsequently be recovered easily. A suitable range for the molar reactant ratio of the N-substituted-α-chloro-ε-caprolactam to caprolactam is about 10:1 to 1:1, a preferred range being from about 5:1 to 1:1. However, the reverse process can also be employed in which a molar ratio in excess of about 2:1 of ε-caprolactam to N-substituted-α-chloro-ε-caprolactam is utilized to obtain a high conversion of N-substituted-α-chloro-ε-caprolactam to α-chloro-ε-caprolactam.

The reaction can be optionally run in the presence of an inert gas such as nitrogen, or other inert gases such as argon, but the presence of an inert gas is not necessary for the success of the reaction.

Percent conversions of the transamidation reaction based on ε-caprolactum are generally in the order of about 80 percent and usually are greater.

The continuous synthesis of α-chloro-ε-caprolactam by a combination of the chlorination of N-substituted-ε-caprolactam and transamidation of N-substituted-α-chloro-ε-caprolactam with ε-caprolactam is a convenient process and also an object of this invention. The chlorination can be conducted using any of the conventional chlorinating agents such as chlorine and sulfuryl chloride, but it is preferred to use sulfuryl chloride because of ease of formation, recovery and recycle. The scope and limitation of the transamidation reaction as utilized in the continuous process are the same as described previously herein.

The process is initiated by chlorinating the N-substituted-ε-caprolactam in a water immiscible inert organic solvent which is also suitable for the transamidation, e.g., a chlorinated aliphatic or aromatic hydrocarbon, preferably ortho-dichlorobenzene, with sulfuryl chloride at a temperature of about 25° to 80° C, preferred temperature of about 40° C. The chlorination of N-substituted-ε-caprolactam proceeds to N-substituted-α-chloro-ε-caprolactam in about 90% conversion after a time period of about 12 to 30 hours. The by-product, sulfur dioxide and hydrochloric acid are vented from the system, the sulfur dioxide collected is reacted with chlorine gas to produce more sulfuryl chloride. ε-Caprolactam is then added to the ortho-dichlorobenzene solution, in which the N-substituted-α-chloro-ε-caprolactam/ortho-dichlorobenzene weight ratio produced is about two and the transamidation is conducted which proceeds in about 85–90% conversion. The α-chloro-ε-caprolactam product is then separated from unreacted N-substituted-α-chloro-ε-caprolactam, ε-caprolactam and N-substituted-ε-caprolactam by conventional methods well known in the art such as fractional crystallization, column chromatography, liquid-liquid extraction or fractional distillation. Preferably, the transamidation solution is cooled to precipitate N-substituted-α-chloro-ε-caprolactam, and then the ortho-dichlorobenzene solution is extracted with dilute aqueous acid, such as hydrochloric acid to recover α-chloro-ε-caprolactam from the process. The filtered N-substituted-α-chloro-ε-caprolactam may be combined with the extracted ortho-dichlorobenzene solution and returned to the chlorination step to initiate the recycle process.

It is intended that the following examples illustrate the spirit of the invention but are not to be construed as limitations on the scope of the invention.

EXAMPLE 1

ε-Caprolactam, 5.65 parts (0.05 mol) and N-benzoyl-α-chloro-εcaprolactam 6.28 parts (0.025 mol) were heated under a nitrogen atmosphere at 140° C. for 4 hours. The reaction mixture was partially analyzed by gas chromatography and found to contain 2.83 parts (0.025 mol) of ε-caprolactam, and 3.69 parts (0.025 mol) of α-chloro-ε-caprolactam.

EXAMPLE 2

Into a 50 ml. three neck flask fitted with a condenser, magnetic stirrer, thermometer and nitrogen inlet tube, were charged 1.13 parts (0.01 mol) ε-caprolactam, 7.55 parts (0.03 mol) N-benzoyl-α-chloro-ε-caprolactam, 4.0 parts xylene, and 1.4 parts (0.00618 mol) hexadecane (a standard for gas chromatographic analysis). The flask was heated in an oil bath at 137° C. for 3 hours while nitrogen was gently bubbled through the reaction mixture. The reaction mixture was analyzed by gas chromatography and found to consist of 4.47 parts (0.0178 mol) of N-benzoyl-α-chloro-ε-caprolactam, 0.2 parts (0.0018 mol) ε-caprolactam, 1.93 parts (0.0089 mol) of N-benzoyl-ε-caprolactam and 1.44 parts (0.00988 mol) α-chloro-ε-caprolactam.

EXAMPLE 3

An 80 ml. pressure tube was charged with 5.65 parts (0.05 mol) ε-caprolactam, 6.3 parts (0.025 mol) N-benzoyl-α-chloro-ε-caprolactam and 5.65 parts toluene. The pressure tube was sealed and heated in an oil bath at 155° C. for 3 hours. The reaction mixture was analyzed by gas chromatography and found to contain 0.7 parts (0.0027 mol) N-benzoyl-α-chloro-ε-caprolactam, 1.935 parts (0.017 mol) ε-caprolactam, 2.38 parts (0.011 mol) N-benzoyl-ε-caprolactam and 2.73 parts (0.0185 mol) α-chloro-ε-caprolactam.

EXAMPLE 4

Apparatus consisting of a 250 ml., three-neck flask fitted with a condenser, magnetic stirrer, thermometer and nitrogen inlet tube, was charged with 11.3 parts (0.1 mol) ε-caprolactam, 50.4 parts (0.2 mols) N-benzoyl-α-chloro-ε-caprolactam and 50 parts xylene. After purging the air in the flask with nitrogen the flask was placed in a 140° C. oil bath for 2 hours. At the end of the reaction interval the flask was cooled, refrigerated overnight and the contents filtered. Recovered were 24.7 parts of solid which analyzed as 85 weight percent N-benzoyl-α-chloro-ε-caprolactam and 14 weight percent N-benzoyl-ε-caprolactam. The mother liquor was extracted with 8 weight percent aqueous hydrochloric acid (4 × 100 ml.) and the resulting acidic aqueous layer was extracted with 3 × 100 ml. of chloroform. Evaporation of the chloroform extract in a rotary evaporator left 11.9 parts of a solid residue which analyzed as 95 weight percent α-chloro-ε-caprolactam and 4 weight percent ε-caprolactam.

EXAMPLE 5

A. Chlorination

Into a suitable reaction vessel 13,500 parts (100 mols) sulfuryl chloride, 27,400 parts (109 mols) N-benzoyl-α-chloro-ε-caprolactam, 21,900 parts (101 mols) N-benzoyl-ε-caprolactam and 27,400 parts of ortho-dichlorobenzene (ODCB) are charged. The contents are heated at about 40° C. for 24 hours. The by-products sulfur dioxide and hydrochloric acid are vented from the reaction vessel and fractionated. The sulfur dioxide, 5760 parts (90 mols) collected is passed with an equimolar amount of chlorine gas through a column packed with activated charcoal for a contact time of a few seconds at a temperature of 25°–30° C. to produce a quantitative yield of sulfuryl chloride.

B. Transamidation

The ODCB solution of N-benzoyl-α-chloro-ε-caprolactam is passed through a charcoal bed to remove tars as impurities. It is then passed into another reaction vessel where 9718 parts (86 mols) of ε-caprolactam are added. The transamidation is conducted by heating and stirring the ODCB solution at 140° C. for 2 hours. The solution is then cooled to 5° C. for 1 hour whereupon 21,000 parts (82 mols) N-benzoyl-α-chloro-ε-caprolactam precipitates out of the solution. The N-benzoyl-α-chloro-ε-caprolactam is filtered off and saved for recycle. The ODCB solution is then extracted with 250,000 parts 8 weight percent aqueous hydrochloric acid to remove α-chloro-ε-caprolactam and residual ε-caprolactam. The aqueous hydrochloric acid is then extracted countercurrently with 250,000 parts chloroform, and the chloroform extract evaporated to yield 10,915 parts (74 mols) of α-chloro-ε-caprolactam and 1356 parts (12 mols) of ε-caprolactam. The ε-caprolactam is separated from the α-chloro-ε-caprolactam by fractional distillation under vacuum and recycled to the transamidation step.

The ODCB solution is then extracted with 250,000 parts 5 weight percent aqueous sodium carbonate to remove acidic impurities and these are discarded. The filtered N-benzoyl-α-chloro-ε-caprolactam is then added to the ODCB solution and then passed to an azeotropic drier where water in the system is azeotropically removed. The dried solution containing 18,662 parts (86 mols) N-benzoyl-ε-caprolactam, 2,065 parts (14 mols) α-chloro-ε-caprolactam and 27,414 parts (109 mols) of N-benzoyl-α-chloro-ε-caprolactam is then pumped to the chlorination vessel, where 3255 parts (15 mols) of makeup N-benzoyl-ε-caprolactam and 13,500 parts (100 mols) sulfuryl chloride are added and the chlorination step repeated as described above.

We claim:

1. A process for preparing α-chloro-ε-caprolactam which comprises reacting N-substituted-α-chloro-ε-caprolactam, wherein the N-substituent is an organic radical selected from the group consisting of aroyl, alkanoyl and arylsulfonyl radicals with ε-caprolactam at a temperature of about 50° to 250° C., thereby forming a reaction mixture containing α-chloro-ε-caprolactam and N-substituted-ε-caprolactam, and recovering the α-chloro-ε-caprolactam from the reaction mixture.

2. The process as recited in claim 1 wherein the N-substituent is an aroyl radical.

3. The process as recited in claim 1 wherein the N-substituent is an alkanoyl radical.

4. The process as recited in claim 1 wherein the N-substituent is an arylsulfonyl radical.

5. The process as recited in claim 2 wherein the aroyl radical is the benzoyl radical.

6. The process as recited in claim 1 wherein the reaction is carried out in the presence of the organic solvent selected from the group consisting of aliphatic ethers, aliphatic hydrocarbons, aromatic ethers, aromatic hydrocarbons, halogenated aliphatic hydrocarbons and halogenated aromatic hydrocarbons.

7. The process as recited in claim 6 wherein the organic solvent is selected from the group consisting of aromatic hydrocarbons and halogenated aromatic hydrocarbons.

8. The process as recited in claim 7 wherein the organic solvent is xylene.

9. The process as recited in claim 7 wherein the organic solvent is ortho-dichlorobenzene.

10. The process as recited in claim 6 wherein the molar ratio of N-substituted-α-chloro-ε-caprolactam to ε-caprolactam is in the range of about 5:1 to 1:1, the weight ratio of organic solvent to N-substituted-α-chloro-ε-caprolactam is in the range of about 5:1 to 1:1 and the temperature is in the range of about 100° to 160° C.

11. The process as recited in claim 10 wherein the N-substituent is the benzoyl radical and the organic solvent is xylene.

12. The process as recited in claim 10 wherein the N-substituent is the benzoyl radical and the organic solvent is ortho-dichlorobenzene.

13. A continuous process for preparing α-chloro-ε-caprolactam which comprises:
   a. reacting an N-substituted-α-chloro-ε-caprolactam, wherein the N-substituent is an organic radical selected from the group consisting of arylsulfonyl, aroyl and perhalogenated alkanoyl radicals, with ε-caprolactam at a temperature of about 50° to 250° C., thereby forming a reaction mixture containing α-chloro-ε-caprolactam and N-substituted-ε-caprolactam;
   b. recovering the α-chloro-ε-caprolactam from the reaction mixture;
   c. chlorinating the remaining reaction mixture containing N-substituted-ε-caprolactam thereby forming N-substituted-α-chloro-ε-caprolactam; and
   d. recycling the N-substituted-α-chloro-ε-caprolactam to (a) for reaction with ε-caprolactam.

14. The process as recited in claim 13 wherein the N-substituent is an aroyl radical.

15. The process as recited in claim 13 wherein the N-substituent is a perhalogenated alkanoyl radical.

16. The process as recited in claim 13 wherein the N-substituent is an arylsulfonyl radical.

17. The process as recited in claim 14 wherein the aroyl radical is the benzoyl radical.

18. The process as recited in claim 13 wherein the reaction is carried out in the presence of an organic solvent selected from the group consisting of aliphatic ethers, aliphatic hydrocarbons, aromatic ethers, aromatic hydrocarbons, halogenated aliphatic hydrocarbons and halogenated aromatic hydrocarbons.

19. The process as recited in claim 18 wherein the organic solvent is selected from the group consisting of aromatic hydrocarbons and halogenated aromatic hydrocarbons.

20. The process as recited in claim 19 wherein the organic solvent is ortho-dichlorobenzene.

21. The process as recited in claim 18 wherein the molar ratio of N-substituted-α-chloro-ε-caprolactam to ε-caprolactam is in the range of about 5:1 to 1:1, the weight ratio of organic solvent to N-substituted-α-chloro-ε-caprolactam is in the range of about 5:1 to 1:1 and the temperature is in the range of about 100° to 160° C.

22. The process as recited in claim 21 wherein the N-substituent is the benzoyl radical and the organic solvent is ortho-dichlorobenzene.

23. The process as recited in claim 22 wherein the clorinating agent is sulfuryl chloride.

* * * * *